US008648049B2

(12) United States Patent  
Zhang et al.

(10) Patent No.: US 8,648,049 B2  
(45) Date of Patent: Feb. 11, 2014

(54) PIGMENT AGGREGATES (75) Inventors: Huaibi Zhang, Palmerston North (NZ); Simon Christopher Deroles, Levin (NZ); Kevin Davies, Manawatu (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 13/265,026

(22) PCT Filed: Apr. 16, 2010

(86) PCT No.: PCT/NZ2010/000073  
§ 371 (c)(1),  
(2), (4) Date: Dec. 15, 2011

(87) PCT Pub. No.: WO2010/123383  
PCT Pub. Date: Oct. 28, 2010

(65) Prior Publication Data  
US 2012/0115800 A1 May 10, 2012

(30) Foreign Application Priority Data  
Apr. 20, 2009 (NZ) ........................................ 576346

(51) Int. Cl.  
*A61K 31/7048* (2006.01)

(52) U.S. Cl.  
USPC ........................................................ 514/27

(58) Field of Classification Search  
USPC ........................................................ 514/27  
See application file for complete search history.

(56) References Cited

U.S. PATENT DOCUMENTS

2008/0300386 A1* 12/2008 Lazarev et al. ............... 530/427  
2011/0263723 A1   10/2011 Deroles et al.

FOREIGN PATENT DOCUMENTS

| JP | 2001-064531 | 3/2001 |
| JP | 2003-164754 | 6/2003 |
| WO | 2009/115023 | 9/2009 |
| WO | 2009/120097 | 10/2009 |

OTHER PUBLICATIONS

Hiroyuki, T. (Nov. 14, 1985) Derwent Abstract Accession No. 1987-183276, JP 62-115069, "Emulsification of anthocyanin colourant to prevent chromophore shift from original reddish purple colour, by adding of surfactant and emulsifying with vegetable oil," 1 page.  
Andersen et al. (2006) "The Anthocyanins," In Flavonoids: Chemistry, Biochemistry and Applications, Eds. A.M. O. and K.R. Markham. CRC Press. pp. 471-551.  
Asen et al. (1975) "Anthocyanin, Flavonol Copigments, and pH Responsible for Larkspur Flower Color," Phytochemistry 14:2677-2682.  
Bligh et al. (1959) "A Rapid Method of Total Lipid Extraction and Purification," Canadian Journal of Biochemistry and Physiology 37(8):911-917.  
Carrapiso et al. (2000) "Development in Lipid Analysis: Some New Extraction Techniques and in situ Transesterification," LIPIDS 35(11):1167-1177.  
Cormier et al. (1993) "XXVII *Vitis vinifera* L. (Grapevine): In Vitro Production of Anthocyanins," In: Bajaj,Y.P.S. (Ed), Biotechnology in Agriculture and Forestry, Medicinal and Aromatic Plants, V. Springer Verlag, Berlin, vol. 24, pp. 373-386.  
Douliez, et al. (2006) "Novel Lipid System Forming Hollow Microtubes at High Yields and Concentration," Langmuir 22:2942-2945.  
Gebauer, et al. (2006) "n-3 Fatty acid dietary recommendations and food sources to achieve essentiality and cardiovascular benefits," American Journal of Clinical Nutrition 83:1526S-1535S.  
Gonnet J-F. (2003) "Origin of the Color of Cv. Rhapsody in Blue Rose and Some Other So-Called 'Blue' Roses," J. Agric. Food Chem. 51:4990-4994.  
Hemleben, V. (1981) "Anthocyanin Carrying Structures in Specific Genotypes of *Matthiola incana* R.Br.," Z. Naturforsch 36c:925-927.  
Jacob et al. (2008) "Physico-Chemical Characteristics of Nanovesicle-Carbohydrate Complexes in Grape Juice Concentrate," Journal of Agricultural and Food Chemistry 56:1305-1315.  
Kubo et al. (1995) "Intravacuolar Spherical Bodies in *Polygonium cuspidatum*," Plant Cell Physiol 36(8):1453-1458.  
Lazaro et al. (1975) "Properties of Spinach Chloroplast Fructose-1,6-Diphosphatase," Phytochemistry 14:2579-2583.  
Liang et al. (2005) "Encapsulation of Lipopeptides Within Liposomes: Effect of Number of Lipid Chains, Chain Length and Method of Liposome Preparation," International Journal of Pharmaceutics 301:247-254.  
Markham et al. (2000) "Anthocyanic Vacuolar Inclusions—Their Nature and Significance in Flower Colouration," Phytochemistry 55:327-336.  
Markham et al. (2004) "Black Flower Coloration in Wild *Lisianthius nigrescens:* Its Chemistry and Ecological Consequences," Z. Naturforsch, Journal of Biosciences 59c:625-630.  
Markham et al. (Aug. 2006) "Separation and Identification of Major Plant Sphingolipid Classes from Leaves," J. Biol Chem 281(32):22684-22694.  
Mulinacci et al. (2001) "Stabilisation of Natural Anthocyanins by Micellar Systems," International Journal of Pharmaceutics 216:23-31.  
Nozzolillo et al. (1988) "An Investigation of the Intracellular Site of Anthocyanins Using Isolated Protoplasts and Vacuoles," Plant Cell Rep 7:389-392.  
Nozue et al. (1995) "Detection and Characterization of a Vacuolar Protein (VP24) in Anthocyanin-Producing Cells of Sweet Potato in Suspension Culture," Plant Cell Physiol 36(5):883-889.

(Continued)

*Primary Examiner* — Wu-Cheng Winston Shen  
*Assistant Examiner* — Yih-Horng Shiao  
(74) *Attorney, Agent, or Firm* — Lathrop & Gage LLP (57) ABSTRACT

The invention provides a method for in vitro formation of anthocyanic vacuolar inclusion (AVI)-like structures, the method comprising the step of combining at least one anthocyanin, and b) at least one lipid. The invention also provides AVI-like structures produced by the method of the invention, compositions comprising such AVI-like structures, and uses of such AVI-like structures.

10 Claims, 5 Drawing Sheets

(56) References Cited

OTHER PUBLICATIONS

Philpott et al. (2009) "Dietary Protection Against Free Radicals: A Case for Multiple Testing to Establish Structure-activity Relationships for Antioxidant Potential of Anthocyanic Plant Species," International Journal of Molecular Sciences 10:1081-1103.

Small et al. (1982) "The Ultrastructure of Anthocyanoplasts in Red-Cabbage," Planta 154:97-99.

Zhang et al. (2006) "New Insight Into the Structures and Formation of Anthocyanic Vacuolar Inclusions in Flower Petals," BMC Plant Biology 6, Art 29, pp. 1-14.

Search Report and Written Opinion, mailed Jul. 28, 2009, corresponding to commonly co-owned International Application No. PCT/NZ2009/000041 (filed Mar. 27, 2009, Deroles et al.), 9 pp.

Conn et al. (2003) "Anthocyanic Vacuolar inclusions (AVIs) selectively bind acylated anthocyanins in *Vitis vinifera* L. (grapevine) suspension culture", Biotechnology Letters 25:835-839, Kluwer Academic Publishers, Netherlands.

Deroles et al. (1998) "An antisense chalcone synthase cDNA leads to novel colour patterns in lisianthus (*Eustoma grandiflorum*) flowers", Molecular Breeding 4:59-66, Kluwer Academic Publishers, Belgium.

Kriat et al. (1993) "Analysis of plasma lipids by NMR spectroscopy: application to modifications induced by malignant tumors," J. Lipid Res. 34:1009-1019.

Morgan, E.R. (1999) "Callus production from protoplasts of *Cyclamen persicum*," Plant Cell, Tissue and Organ Culture 55:63-65, Kluwer Academic Publishers, Netherlands.

Nozue et al. (1993) "Characterization of Intravacuolar Pigmented Structures in Anthocyanin-Containing Cells of Sweet Potato Suspension Cultures", Plant Cell Physiol. 34(6):803-808.

* cited by examiner

PIGMENT AGGREGATES

CROSS-REFERENCE TO RELATED APPLICATIONS

This application is a U.S. National Stage Application under 35 U.S.C. §371 of International Application No. PCT/NZ2010/000073, filed Apr. 16, 2010 and published in English on Oct. 28, 2010 as WO 2010/123383, which claims the benefit of New Zealand Application 576346, filed Apr. 20, 2009. Both of these applications are hereby incorporated by reference in their entireties.

TECHNICAL FIELD

The invention relates to an in vitro method for the production of pigment structures and compositions, preferably from plant-derived components, and to applications of such pigment structures and compositions.

BACKGROUND ART

In recent years, demand for natural colourants has been steadily increasing in the food and beverage industry due to consumers' concerns about synthetic colourants. Anthocyanins are natural compounds that are synthesised in plants and can offer a wide range of colours. Anthocyanins are among the most preferred natural colourants because they function not only as natural colourants and but have antioxidant properties, and have been shown in many studies to have health-promoting effects.

Anthocyanins are the most significant flavonoid pigments. They are based on a core 15-carbon (C15) structure of two aromatic rings (the A and B rings) joined by a third ring of three carbons and one oxygen (the C-ring) (Andersen and Jordheim 2006). The anthocyanin is formed by glycosylation of a core anthocyanidin structure—in the great majority of cases the initial O-glycosylation is at the C-3 position. Additional modification by hydroxylation, acylation, methylation and further glycosylation generates the large number of known anthocyanin variant structures. Although over 30 different core anthocyanidins have been identified, the six common ones (pelargonidin, cyanidin, peonidin, petunidin, malvidin) are the basis of about 90% of the known anthocyanins. Some of the less common anthocyanidins contribute important flower pigments in a small number of species, such as the 3-deoxyanthocyanins and 6- and 8-hydroxyanthocyanins.

However, the low stability of anthocyanins during and after extraction from plants and when added to food or beverage products is a major hurdle for commercially utilizing anthocyanins as colourants. In plants, anthocyanins are a subclass of flavonoids that are widely present in many species. Anthocyanins are synthesised in a branch of the flavonoid biosynthesis pathway. Upon biosynthesis, anthocyanins are usually transported into and stored in the central vacuole of the plant cell. Under the vacuolar conditions, anthocyanins are usually positively charged and present in coloured forms. In the vacuole, anthocyanins accumulate in a soluble form and/or as anthocyanic vacuolar inclusions (AVIs) (Markham et al. 2000).

In comparison with completely soluble anthocyanins, AVIs can be highly stable under wide range of conditions (unpublished data). Some of these conditions are compatible with food and beverage products. Therefore, use of AVIs in food and beverage products could be an effective way to utilise anthocyanins as natural colourants in such products.

However, extraction of AVIs from plants in sufficient quantities for use in food, beverage and other products, may be limited by the efficiency of purification procedures and quantity of the appropriate AVI-containing plant material available.

It would therefore be beneficial to develop methods for stabilising anthocyanins in a form similar to AVI from more readily available/or more easily purifiable components.

It is therefore an object of the invention to provide a method for producing AVI-like structures in vitro.

SUMMARY OF THE INVENTION

In a first aspect the invention provides a method for in vitro formation of anthocyanic vacuolar inclusion (AVI)-like structures, the method comprising the step of combining
a) at least one anthocyanin, and
b) at least one lipid.

Anthocyanin

Any anthocyanin may be used in the method of the invention.

In one embodiment the anthocyanin is a glycoside of an anthocyanidin.

Anthocyanidin Types

In one embodiment the anthocyanidin is selected from one of: cyanidin, peonidin, delphinidin, pelargonidin, petunidin, malvidin, 3-deoxyathocyanindins, and 6- and 8-hydroxyanthocyanidins, and hydroxylated, acylated, and methylated derivatives thereof.

In a preferred embodiment the anthocyanidin is selected from one of: cyanidin, peonidin, delphinidin, and pelargonidin, and hydroxylated, acylated, and methylated derivatives thereof.

In a preferred embodiment the acylation is aromatic acylation.

Glycoside Types

In one embodiment the anthocyanin is a glucoside of an anthocyanidin.

In a further embodiment the anthocyanin is a galactoside of an anthocyanidin.

In a further embodiment, the anthocyanin is a monoglycoside of the anthocyanidin.

In a further embodiment, the anthocyanin is a diglycoside of the anthocyanidin.

In a further embodiment the anthocyanin is an acylated glycoside of the anthocyanidin.

In a further embodiment, the anthocyanin is an acylated monoglycoside of the anthocyanidin.

In a further embodiment, the anthocyanin is an acylated diglycoside of the anthocyanidin.

In a further embodiment the anthocyanin has O-glycosylation at one or more of the 3-, 5-, 7-, 3'- or 5' positions.

In a preferred embodiment the anthocyanin has O-glycosylation and acylation at one or more of the 3-, 5-, 7-, 3'- or 5' positions.

In a more preferred embodiment the anthocyanin is a 3- or 5-O-glycoside.

In a more preferred embodiment the anthocyanin is a 3,5-di-O-glycoside.

In a more preferred embodiment the anthocyanin is a 3,5-di-O-glycoside with acylation.

In one embodiment the pigment composition comprises at least one anthocyanin selected from those listed in Table 2.

In a further embodiment the pigment composition comprises at least one anthocyanin selected from those from lisianthus listed in Table 2.

In a preferred embodiment the acylation is aromatic acylation.

In one embodiment the anthocyanin is pelargonidin-3-glucoside (Pel-3-G).

A mixture of different anthocyanins, including at least one type as discussed above (the first anthocyanin), and one or more additional anthocyanins, may also be used in the method of the invention.

In one embodiment the additional anthocyanin/s is of a type discussed above, but different from the first anthocyanin.

Lipid

Any lipid may be used in the method of the invention.

In one embodiment the lipid is from a biological source.

In one embodiment the biological source is selected from animals, fish or plants.

In one embodiment the lipid is extracted from a biological membrane or biomembrane.

In one embodiment the lipid is used in the method of the invention as part of a biological membrane or biomembrane.

In a preferred embodiment the lipid is from a plant cell or plant.

In a preferred embodiment the lipid is a fatty acid.

In a preferred embodiment the fatty acid is an Ω-3 fatty acid.

In one embodiment the lipid is a glycerolipid.

In a further embodiment the lipid is monogalactosyldiacylglycerol (MGDG).

In a further embodiment the lipid is digalactosyldiacylglycerol (DGDG).

In a further embodiment the lipid is a glycerophospholipid.

In a further embodiment the lipid is a sphingolipid.

In a further embodiment the lipid is a saccharolipid.

In a further embodiment the lipid is a polyketide.

In a further embodiment the lipid is a sterol lipid.

In a further embodiment the lipid is a prenol lipid.

In a further embodiment the lipid is sulphoquinovosyldiacylglycerol.

A mixture of different lipids, including at least one type as discussed above (the first lipid), and one or more additional lipids, may also be used in the method of the invention.

In one embodiment the additional lipid is of a type discussed above, but different from the first lipid.

Conditions for Combining the Anthocyanin and the Lipid

In a further embodiment the anthocyanin and the lipid, are dissolved in a solvent, prior to formation of the AVI-like structure.

In one embodiment the solvent is a polar aprotic solvent.

In one embodiment the polar aprotic solvent is selected from dimethyl sulfoxide, dimethylformamide, dioxane and hexamethylphosphorotriamide, tetrahydrofuran.

In a further embodiment the solvent is a mixture of chloroform and methanol. Preferably pH is optomised.

In a further embodiment the solvent is a mixture of chloroform and ethanol. Preferably pH is optomised.

In a preferred embodiment the solvent is DMSO.

In a preferred embodiment the DMSO is at least 10%, more preferably at least 20%, more preferably at least 30%, more preferably at least 40%, more preferably at least 50%, more preferably at least 60%, more preferably at least 10%, more preferably at least 80%, more preferably at least 90%, v/v with water. In a most preferred embodiment the solvent is a pure DMSO.

In one embodiment the solution containing the anthocyanin and the lipid is centrifuged to remove non-dissolved material.

In a further embodiment the solution containing the anthocyanin and the lipid is concentrated, prior to formation of the AVI-like structure.

In one embodiment the solution is concentrated by evaporating at least some of the solvent.

In a further embodiment the solvent is evaporated by vacuum evaporation.

In one embodiment the AVI-like structure is formed in an aqueous solution.

In one embodiment the aqueous solution contains salt.

In one embodiment the salt is NaCl.

In a further embodiment the aqueous solution contains NaCl in the range 1 mM to 500 mM, preferably in the range 10 mM to 400 mM, more preferably in the range 20 mM to 300 mM, more preferably in the range 30 mM to 200 mM, more preferably 40 mM to 100 mM, more preferably 50 mM to 80 mM, most preferably 50 mM to 60 mM.

In an alternative embodiment the AVI-like structure is formed in a lipid-based environment.

In a further embodiment the AVI-like structure is formed in an acid-based solution.

In a further embodiment the AVI-like structure is formed in a pH range between pH 0.1 and pH 6.9, preferably between 1.0 and 6.5, more preferably between 2.0 and 6.0, more preferably between 3.0 and 5.5, more preferably between 4.0 and 5.5. Most preferably the structure is formed at a pH of about 5.0.

In a further embodiment pH-adjusting acids include, but are not limited to, lactic acid, acetic acid, formic acid, citric acid, malonyl acid, oxalic acid, citric acid, malic acid, tartric acid, tannic acid, benzoic acid, butyric acid, hydrochloric acid, phosphoric acid and sulfuric acid.

In one embodiment the acid-based solution is an acetic acid solution.

In a further embodiment the acetic acid is in the range 0 to 1.0M, preferably in the range 0.2 to 0.8M, more preferably in the range 0.2 to 0.6M, more preferably in the range 0.3 to 0.5M, most preferably 0.4M acetic acid.

AVI-Like Structure Produced by the Method of the Invention

In a further aspect the invention provides au AVI-like structure produced by the method of the invention.

Stability of AVI-Like Structure

In one embodiment the AVI-like structure is stable at acidic pH and 4° C. for at least about 24 hours, preferably at least about 72 hours, more preferably at least about 120 hours, more preferably at least about 240 hours, most preferably at least about 360 hours.

In a further embodiment the AVI-like structure is stable at acidic pH and 25° C. for at least about 24 hours, preferably at least about 72 hours, more preferably at least about 120 hours, more preferably at least about 240 hours most preferably at least about 360 hours.

In a further embodiment the AVI-like structure is stable at acidic pH and 37° C. for at least about 24 hours, preferably at least about 48 hours, more preferably at least about 72 hours, most preferably at least about 120 hours.

Preferably the AVI-like structure is stable over a pH range from about 2.5 to about 8.0, preferably from about 4.0 to about 7.0, most preferably from about 5.0 to about 6.0.

In a further embodiment the AVI-like structure is stable under high light intensity for at least about 48 hours, preferably at least about 72 hours, more preferably at least about 120 hours, most preferably at least about 168 hours.

Preferably high light intensity refers to light intensity of greater than about 10 umoles photons per m2 per sec, more preferably greater than about 50, most greater than about 90.

The stability of and AVI-like structure of the invention my refer to the stability of the anthocyanin in the AVI-like structure, or the stability of the lipid in the AVI-like structure, or both.

Stability of Anthocyanin in the AVI-Like Structure

Stability of the anthocyanin in the AVI-like structure preferably refers to the rate of loss of anthocyanic.

Preferably the anthocyanin is more stable (retains more colour) when part of the AVI-like structure, than when not part the AVI-like structure, such as when in solution.

Preferably the anthocyanin in the AVI-like structure retains of at least 50% (more preferably at least 60%, more preferably at least 70%, more preferably at least 80%, more preferably at least 90%) of the its colour (as defined by optical density at 530 nm) under the specified conditions.

Stability of the Lipid in the AVI-Like Structure

Stability of the lipid preferably refers to the rate of oxidation of the lipid.

Preferably the lipid is more stable (less susceptible to oxidation) when part of the AVI-like structure, than when not part the AVI-like structure, such as when in solution.

In one embodiment the AVI-like structure prevents 50% of the double bonds, in the fatty acids being attacked by oxygen.

In a further embodiment the AVI-like structure prevents 60% of the double bonds in the fatty acids being oxidised.

In a further embodiment the AVI-like structure prevents 70% of the double bonds in the fatty acids being oxidised.

In a further embodiment the AVI-like structure prevents 80% of the double bonds in the fatty acids being oxidised.

In a further embodiment the AVI-like structure prevents 90% of the double bonds in the fatty acids being oxidised.

In a further embodiment the AVI-like structure prevents 95% of the double bonds in the fatty acids being oxidised.

In a preferred embodiment the AVI-like structure prevents 100% of the double bonds in the fatty acids being oxidised.

Preferably the AVI-like structure prevents at least 50%, more preferably at least 60%, more preferably at least 70%, more preferably at least 80%, more preferably at least 90%, more preferably at least 95%, of the double bonds in the fatty acids being attacked by oxygen.

Compositions and Products Comprising an AVI-Like Structure of the Invention

In a further aspect the invention provides a composition comprising an AVI-like structure of the invention.

In one embodiment the composition comprises an AVI-like structure and an acceptable carrier.

In a further aspect the invention provides a food product comprising an AVI-like structure of the invention.

In a further aspect the invention provides a beverage comprising an AVI-like structure of the invention.

In a further aspect the invention provides a cosmetic product comprising an AVI-like structure of the invention.

In a further aspect the invention provides fabric coloured with an AVI-like structure of the invention.

In a further aspect the invention provides a topical cream comprising an AVI-like structure of the invention.

In a further aspect the invention provides a nutraceutical or pharmaceutical product comprising an AVI-like structure of the invention.

In one embodiment the lipid used to form the AVI-like structure in the nutraceutical or pharmaceutical is a lipid capable of providing health benefits.

In one embodiment the lipid is a fatty acid.

In a preferred embodiment the fatty acid is an Ω-3 fatty acid.

Methods of Use of the AVI-Like Structures of the Invention

In a further embodiment the invention provides a method for delivering an anthocyanin to a subject who would benefit from the anthocyanin, the method comprising delivery of the anthocyanin in the form of an AVI-like structure of the invention.

In a further embodiment the invention provides a method for delivering a lipid to a subject who would benefit from the lipid, the method comprising delivery of the lipid in the form of an AVI-like structure of the invention.

In one embodiment the lipid is a fatty acid.

In a preferred embodiment the fatty acid is an Ω-3 fatty acid.

In a further embodiment the invention provides a method for improving the health of a subject, the method comprising delivery of an AVI-like structure of the invention to the subject.

In a further embodiment the invention provides a method of treating ill health in a subject subject, the method comprising delivery of an AVI-like structure of the invention to the subject.

In a further embodiment the invention provides use of an AVI-like structure of the invention to improve the health of a subject.

In a further embodiment the invention provides use of an AVI-like structure of the invention to treat ill health.

In a further embodiment the invention provides use of an AVI-like structure of the invention in the preparation of a medicament to improve the health of a subject.

In a further embodiment the invention provides use of an AVI-like structure of the invention in the preparation of a medicament to treat ill health.

Ill health may be poor nutritional status.

Ill health may be sub-optimal nutritional status.

To improve health may be to improve nutritional status.

DETAILED DESCRIPTION OF THE INVENTION 1.0 General Definitions

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

2.0. AVIs

Anthocyanin pigments most commonly accumulate in the plant cell vacuole and are responsible for many of the colours in petals and fruits within the red to blue range. In most plant species the anthocyanins remain in solution and are evenly distributed within the vacuole. However in some species the anthocyanins are aggregated into small bodies within the vacuole, which enhances the cells ability to accumulate large amounts of anthocyanin. These anthocyanin-containing bodies have been described under several different names in a range of plant tissues as shown in Table 1. Such anthocyanin-containing bodies are referred to here as "anthocyanic vacuolar inclusions" or "AVIs".

TABLE 1

| Plant Species and Tissue | Description | Reference |
|---|---|---|
| Rose petals | AVIs | Gonnet, 2003 |
| *Polygonium cuspidatum* seedlings | Intravacuolar spherical bodies | Kubo et al., 1995 |
| *Matthiola incana* petals | Crystals | Hemleben, 1981 |
| *Consolida ambigua* petals | Blue crystals | Asen et al., 1975 |
| Mung bean hypocotyl | Red crystals | Nozzolillo and Ishikura, 1988 |
| Red cabbage leaves | Anthocyanoplasts | Small and Pecket, 1982 |
| *Ipomea batatas* tubers | Cyanoplasts | Nozue et al., 1995 |
| Grape cell cultures | Anthocyanoplasts | Cormier and Do, 1993 |

AVIs have also been described by Markham et al., (2000) and Zhang et al., (2006). The same papers describe methods for the isolation of AVI's from Purple lisianthus (*Eustoma grandiflorum*) and the Blue-grey carnation (*Dianthus caryophyllus*) and are incorporated herein by reference.

AVIs are globular or irregular in shape. AVIs display different colours according to their anthocyanin composition.

The applicants have elucidated the structure/composition of AVIs. The applicants have shown that anthocyanins and lipids are the two main classes of compounds found in the AVIs.

Preferably the term "anthocyanic vacuolar inclusion" or "AVI" as used herein means a structure found in the vacuole in a plant, comprising an anthocyanin and a lipid.

AVIs may comprise biological membranes or biomembranes that include lipids, proteins and sugar groups.

Preferably, the anthocyanin is more stable when part of the AVI, than when not part of the AVI, such as when in solution.

Preferably, the lipid is more stable when part of the AVI, than when not part of the AVI, such as when in solution.

Typically both the anthocyanin and the lipid are more stable when forming part of an AVI than they are when either the anthocyanin or lipid are separate, such as in solution.

AVIs are typically composed of single or multiple forms of anthocyanin molecules that are bound to by a lipid (such as a fatty acids or biomembranes), where such an interaction results in the increased stability of both the anthocyanins and the lipid.

The term "stable" in relation to anthocyanins in AVIs, refers to a reduced rate of loss of anthocyanic colour in environments normally associated with a loss of anthocyanic colour. Preferably stable refers to retention of at least 50% (more preferably at least 60%, more preferably at least 70%, more preferably at least 80%, more preferably at least 90%) of the anthocyanin's colour (as defined by optical density at 530 nm) under the specified conditions.

The term "stable" in relation to lipids in AVIs refers to prevention of lipid-oxidation under the specified conditions.

3.0 AVI-Like Structures of the Invention

The present invention relates to in vitro methods for forming AVI-like structures, and to uses of such in vitro produced AVI-like structures.

As used here in the term "anthocyanin vacuolar structure", or "AVI-like structure", means a structure that is produced in vitro by combining at least one anthocyanin and at least one lipid.

The terms "anthocyanin vacuolar inclusion-like structure (AVI-like structure)" and "anthocyanin vacuolar inclusion-like aggregate (AVI-like aggregate)" have the same meaning and can be used interchangably.

3.1 Appearance of the AVI-Like Structures of the Invention

The AVI-like structures of the invention have an appearance substantially similar to AVIs found in plants or isolated from plants.

In one embodiment the AVI-like structures of the invention are not identical to AVIs found in plants or isolated from plants.

The AVI-like structures of the invention can be round or irregular and aggregate-like.

The AVI-like structures are typically in the size range 100 µm-1 nm, preferably 50 µm-1 nm, more preferably 10 µm-1 nm, more preferably 5 µm-1 nm.

Size of the AVI-like structures can be controlled during or after formation to suit their intended use. Size may be controlled by physical methods such as sonication.

3.2 Stability of the AVI-Like Structures of the Invention

AVI-like structures preferably show at least substantially similar stability to AVIs found in or isolated from plants.

The term "stable" in relation to anthocyanins in AVI-like structures, or AVI-like structure containing compositions or products, refers to a reduced rate of loss of anthocyanic colour in environments normally associated with a loss of anthocyanic colour. Preferably stable refers to retention of at least 50% (more preferably at least 60%, more preferably at least 70%, more preferably at least 80%, more preferably at least 90%) of the anthocyanin's colour (as defined by optical density at 530 nm) under the specified conditions.

The term "stable" in relation to lipids in the AVI-like structures or AVI-like structure containing composition or products, refers to prevention of lipid oxidation under the specified conditions.

4.0 Anthocyanins for Use in the Method of Producing the AVI-Like Structures of the Invention The term "anthocyanins" means glycosides of any of anthocyanidins, including but not limited to, pelargonindin, cyanidin, peonidin, delphinidin, petunidin, malvidin, 3-deoxyathocyanindins, and 6- and 8-hydroxyanthocyanidins, and hydroxylated, acylated, and methylated derivatives thereof. Preferably the glycosides are glucosides or galactosides. Preferably the acylation is aromatic acylation.

Preferably, the anthocyanin has O-glycosylation at one or more of the 3-, 5-, 7-, 3'- or 5' positions, more preferably the anthocyanin has O-glycosylation and acylation at one or more of the 3-, 5-, 7-, 3'- or 5' positions, more preferably the anthocyanin is a 3- or 5-O-glycoside, more preferably the anthocyanin is a 3,5di-O-glucoside, and most preferably the anthocyanin is a 3,5-di-O-glycoside with acylation. Preferably the acylation is aromatic acylation.

4.1 Source of Anthocyanins for Use in the Method of the Invention

Anthocyanins for forming AVI-like structures of the invention in vitro may be extracted from AVI-containing plant materials or non-AVI-containing plant materials. These anthocyanins may be extracted by methods known to those skilled in the art.

4.1.1 Isolation of Anthocyanins from Non-AVI-Containing Plants, for Use in the Invention Anthocyanins may be isolated from plants, including non-AVI containing plants by methods known to those skilled in the art such as but not limited to those described by (Markham et al. 2004; Markham et al. 2000).

4.1.2 Isolation of Anthocyanins from AVI-Containing Plants, for Use in the Invention Anthocyanins may be isolated from AVI-containing plants. It may be beneficial to first isolate the AVIs, before extracting the anthocyanin.

AVIs may be isolated from plant materials using various methods (Markham et al, 2000; Zhang, et al, 2006).

An example of AVI isolation procedure is described below:

1) Plant material that contains AVIs, preferably, flower petals, are washed thoroughly with tap water containing surface disruption agent, such as Tween-20, to remove contaminating materials. To remove the remaining Tween 20-like agent, the plant material is rinsed with tap water.
2) The washed plant material is subsequently mechanically macerated until it becomes a slurry using any cutting devices in a small amount of suitable buffers such as phosphate buffer (0.1 M, Ph 7.0). The buffers may contain EDTA (10 mM).
3) The slurry is then enzymatically macerated to release protoplasts using a solution containing 1% (w/v) cellulase Onozuka R-10 (Yakult Honsha Co., Higashi-Shinbashi, Minatoku, Tokyo) and 0.05% (w/v) pectolase Y23. The enzymatic maceration was carried out overnight at room temperature.
4) AVI-containing protoplasts are enriched by filtering the enzymatically macerated slurry through cheese cloth or metal screens their pore sizes allow AVI containing protoplasts to pass. The AVI-containing protoplasts are then washed with buffers in which any released AVIs are stable, for example, 0.1 phosphate buffer containing 17.53 g/L sodium chloride. The AVI-containing protoplasts are then concentrated into a loose pellet by centrifuging.
5) The AVI-containing pellet is then transferred into 80% (v/v) percoll (AMRAD-Pharmacia Biotech, Auckland, New Zealand). AVIs are released from the protoplasts by vortexing or gentle ultrasonic suspension treatment.

Anthocyanins may be isolated from the AVIs by extraction with 80% methanol containing 5% acetic acid.

4.1.3 Commercial Sources of Anthocyanins, for Use in the Invention

Anthocyanins are commercially available from several sources including: Sensient Technologies (www.sensient-tech.com), Christian Hansen (http://www.chr-hansen.com/), Diana-Naturals (www.diana-naturals.com/), Aarkay Food Products Ltd (http://www.aarkayfoods.in), Shanghai Richem International Co.; Ltd (http://www.srichem.com), Hangzhou New Asia International Co., Ltd. (www.herbalsextract.com), and DaXingAnLing Lingonberry Organic Foodstuffs Co., Ltd. (http://www.lgberry.com.cn)

5.0 Lipids for Use in the Invention

Any suitable lipid may be used in the method of the invention.

The term "lipid" as used herein includes: fatty acids, detergents, fats, oils, waxes, phospholipids, glycolipids, sulfoquinovosyldiacylglycerol, eicosonoids, terpenes, steroids and lipid soluble vitamins.

The lipid may be extracted from a biological membrane or biomembrane.

The lipid may be used in the invention as part of a biological membrane or biomembrane.

Term "biological membrane" or "biomembranes" means any cellular membranes or synthetic membranes consisting of lipids, optionally proteins and optionally sugar groups. Preferably the membranes are plant cellular membranes, more preferably plant vacuolar membranes.

The lipid may be a fatty acid. A preferred fatty acid is an $\Omega$-3 fatty acid.

The lipid may also be selected from the group comprising but not limited to a glycerolipid, a monogalactosyldiacylglycerol (MGDG), digalactosyldiacylglycerol (DGDG), a glycerophospholipid, a sphingolipid, a saccharolipid, a polyketide, a sterol lipid, a prenol lipid; and a sulphoquinovosyldiacylglycerol.

5.1 Source of Lipids, for Use in the Invention

Lipids may be prepared by synthetic methods known to those skilled in the art (Douliez, et al. 2006; Liang et al. 2005).

The lipids may also be isolated, using various methods, from any biological materials.

Preferably the biological material is plant material.

5.2 Isolation of Lipids from Plants, for Use in the Invention

Lipids may be isolated from plants including non-AVI-containing plants by methods known to those skilled in the art (Bligh and Dyer, 1959, Carrapiso and Garcia, 2000; Markham et al. 2006).

Lipids for use in the invention may also be isolated from AVIs that have been purified from AVI-containing plants. AVIs may be purified as described above under section 4.1.2.

Isolation of from isolated AVIs may, for example, be carried out using an organic solvent, such as chloroform:methanol:TFA (50:50:0.5 v:v:v). Freeze-dried AVIs may be dissolved with the organic solvent. Subsequently, the organic solvent containing dissolved AVIs may be partitioned against acidified water. This partitioning process may be repeated several times. The resultant aqueous phases are then combined for anthocyanins. The organic phase contains lipids, and subsequently, the lipid-containing phase may be dried under nitrogen to prepare lipids.

Lipids may also be extracted from purified AVIs using, for example, an organic solvent such as chloroform:methanol:TFA (50:50:0.5 v:v:v).

5.3 Isolation of Biomembranes from Plants

Membranes may isolated by various methods. For example, membranes may be isolated from biological sources, particularly from plant materials (Graham and Higgins, 1993).

5.4 Synthetically Produced Membranes

Membranes may be created by microvesicles through mixing various different lipids. The membranes or microvesicles may be prepared by methods known to those skilled in the art (Graham and Higgins, 1993).

5.5 Commercial Sources of Lipids

Lipids from commercial sources may also be used in methods of the invention.

Suitable lipids are available from various commercial sources including but not limited to Sigma-Aldrich (3050 Spruce St., St. Louis, Mo. 63103, USA) Lipid Products (Nutfield Nurseries, Crab Hill Lane, South Nutfield, Redhill, Surrey, RH1 5PG, England).

6.0 Compositions Comprising AVI-Like Structures

The invention also provides compositions comprising AVI-like structures.

In one embodiment the compositions additionally comprise an acceptable carrier.

The term "acceptable carrier" with reference to the composition of the invention means a component, additional to the AVI-like structure itself, which is acceptable for the composition's application. Acceptable carriers include but are not limited to solvents, buffers and preservatives.

Acceptable carriers for use in the composition for food product applications are known to those skilled in the art and include but are not limited to:

Water-Soluble Carriers:

Gums, Carrageenan, Gum Arabic, Alginates, Ammonin alginate, Potassium alginate, Sodium alginate, Starches, Maltodextrins, Sucrose, Dextrose, Fructose, Syrups, Alcohols, Glycerol, Sodium carbonate, Sodium hydrogen carbonate, Ethyl cellulose, Microcrystalline cellulose, Cellulose, Powdered Benzyl alcohol, Ethyl Alcohol (ethanol), Ethyl Acetate, Lactose starch, Citric Acid, Diethyl Tartrate, Lactic acid ethyl ester, Magnesium Carbonate, Magnesium Hydrogen Carbonate, Polydextrose, Polyethylene Glycol, Polyoxyethylene (20) Sorbitan Monolaurate, Polyoxyethylene (20) Sorbitan Monooleate, Polyoxyethylene (20) Sorbitan Monopalmitate, Polyoxyethylene (20) Sorbitan Monostearate, Polyoxyethylene (20) Sorbitan Tristearate, Polyvinylpyrrolidone, Propan-2-Ol, Propylene glycol, and Silicon Dioxide.

Oil Soluble Carriers:

Edible fats and oils, Medium chain triglycerides, Bees' wax, Paraffin, Shellac, Rosin, 6-Palmitoyl-L-ascorbic acid, Amyl Acetate, Butane-1,3-Diol, Diethylene Glycol Monoethyl Ether, Isopropyl Myristate, Triacetin, and Ethyl Citrate.

Acceptable carriers for use in the composition for cosmetic product applications are known to those skilled in the art.

Acceptable carriers for use in the composition for textile colouring applications are known to those skilled in the art.

7.0 Preparation of the Pigment Compositions of the Invention

The composition comprising an AVI-like structure may be prepared by methods known to those skilled in the art.

For example, the composition can be sold as an additive for food or other products and can be prepared in dry, e.g., powdered, form or as a water or alcohol-based concentrate or syrup depending on the end use and the proposed method of addition.

The size of the AVI-like structure may be manipulated by physical means, for example sonification, to suit the application, and/or to promote suspension or distribution in a liquid, semisolid, pulp, cream or solid product.

The AVI-like structure, or composition, of the invention may be added to food products by methods known in the art.

The AVI-like structure, or composition, may be combined with one or more spray drying aids such as gum arabic and maltodextrins or the solution may be encapsulated by standard coascervation techniques in edible materials using gelatin.

The AVI-like structure, or composition, may be added in conjunction with other materials such as flavouring adjuvants.

The AVI-like structure, or composition, can be incorporated as a solid or an aqueous solution or syrup at various stages during the manufacture Or processing of the food product.

The AVI-like structure, or composition, can be incorporated to food and beverage products in many ways, such as but not limited to:

- direct mixing via batch (tanks/blenders), using rotational impellers in aqueous materials.
- continuous or inline mixers in aqueous materials.
- dry blending into convenience foods for reconstitution by the consumer.
- coating the exterior surfaces of products through spraying, enrobing, and pan coating.

The AVI-like structure, or composition, may need to be pre-dissolved in water to ensure maximum dispersibility and even mixing during food and beverage product manufacture. Small amounts of highly concentrated AVI-like structures or compositions may be dispersed in icings (sugar/fat blends).

Due to their stable nature, the AVI-like structures, or compositions, can be added to the early stages of production, ensuring they are distributed evenly, while maintaining optimal visual appeal.

The AVI-like structures or compositions can be used in combination with other food colouring materials to obtain the desired colour in the finished product.

8.0 Products Comprising AVI-Like Structures, or Compositions, of the Invention The term "food product" as used herein includes solid foods, liquid beverages and other edible materials regardless of their specific form. The term food product includes products that are chewed without being swallowed. Preferred food products include but are not limited to dairy products, such as yoghurts.

The present invention is not limited to use of the AVI-like structures or compositions in food products. Use of AVI-like structures or compositions to colour other products such as fabrics, and particularly products such as clothing and cosmetics that come into human contact, are included within the scope of the invention.

EXAMPLES

Example 1

Isolation of AVIs from Carnation and Lisianthus

Plant Material

Carnation (a mauve coloured cultivar of *Dianthus caryophyllus*) or Lisianthus (#54 cultivar of *Eustoma grandiflorum*) were grown in the glasshouse under the conditions of natural lighting and day length. Fully expanded flower petals were collected and washed to remove unwanted contaminants.

Carnation AVIs are more round-shaped throughout the petal than the more irregular shaped AVIs of lisianthus. Carnation AVIs are found throughout the petals. The structure of AVIs was previously unknown. The applicants hypothesised that although AVIs do not have surface membranes to contain them, they may have infrastructural membranes or lipids. The applicants have now shown that anthocyanins are the two major components of AVIs as described below.

AVIs were isolated as follows:

Protoplast Preparation

1) The washed flower petals were mechanically macerated using an onion chopper or razor-blade to form a slurry. Subsequently, the slurry was incubated in an enzyme solution comprising 1% cellulase Onozuka R-10 (Yakult Honsha Co., Higashi-Shinbashi, Minatoku, Tokyo) and 0.05% pectolase Y23 (Morgan, 1998). The enzymatic maceration was carried out overnight at room temperature.

2) AVI-containing protoplasts were enriched by filtering the enzymatically macerated slurry through cheese cloth or metal screens with pore sizes that allow AVI containing protoplasts to pass. The AVI-containing protoplasts were then washed with buffers in which any released AVIs are stable, for example, 0.1 phosphate buffer containing 17.53 g/L sodium chloride. The AVI-containing protoplasts were then concentrated into a loose pellet by centrifuging.

3) The AVI-containing pellet was then transferred into 80% percoll (AMRAD-Pharmacia Biotech, Auckland, New Zealand). AVIs were released from the protoplasts by vortexing or gentle ultrasonic suspension treatment.

Example 2

Elucidation of the Structure of AVIs

Anthocyanin Analysis

For anthocyanin analysis, the AVIs, prepared according to the procedures described above, were extracted with 80% methanol with 5% acetic acid. The extract was then subjected to LC-MS analysis. Table 2 below listed the anthocyanins found in the carnation and lisianthus AVIs.

TABLE 2

| | [M + H]+ |
|---|---|
| Lisianthus AVIs (purple) | |
| Cyanidin-3-O-glucoside | 449 |
| Delphinidin-3-O-glucoside | 465 |
| Cyanidin-3-O-galactoside-5-O-(6-O-p-coumaroylglucoside) | 757 |
| Cyanidin-3-O-galactoside-5-O-(6-O-ferulylglucoside) | 787 |
| Delphinidin-3-O-galactoside-5-O-(6-O-p-coumaroylglucoside) | 773 |
| Delphinidin-3-O-galactoside-5-O-(6-O-ferulylglucoside) | 803 |
| Cyanidin-O-coumaroylglucoside | 595 |
| Delphinidin-O-coumaroylglucoside | 611 |
| Delphinindin-3-O-acetylglucoside-5-O-glucoside(or galactoside) | 669 |
| Peonidin-3-O-rhamnogalactoside-5-O-(6-O-p-coumaroylglucoside) | 813 |
| Delphinidin-3-O-galactoside-5-O-(6-O-p-coumaroylglucoside) + m/z 123 | 896 |
| Cyanidin-3-O-galactoside-5-O-(6-O-p-coumaroylglucoside) + m/z 155 | 912 |
| Delphinidin-3-O-rhamnogalactoside-5-O-(6-O-p-coumaroylglucoside) | 919 |
| Cyanidin-3-di-O-galactoside-5-O-(6-O-p-coumaroylglucoside) | 919 |
| Delphinidin-3-O-galactoside-5-O-(6-O-ferulylglucoside) + m/z 123 | 926 |
| Delphinidin-3-di-O-galactoside-5-O-(6-O-p-coumaroylglucoside) | 935 |
| Cyanidin-3-O-galactoside-5-O-(6-O-ferulylglucoside) + m/z 155 | 942 |
| Delphinidin-3-O-rhamnogalactoside-5-O-(6-O-ferulylglucoside) | 949 |

TABLE 2-continued

| | [M + H]+ |
|---|---|
| Cyanidin-3-di-O-galactoside-5-O-(6-O-ferulylglucoside) | 949 |
| Delphinidin-3-di-O-galactoside-5-O-(6-O-ferulylglucoside) | 965 |
| Pelargonidin-3-O-galactoside-5-O-(6-O-p-coumaroylglucoside) | 741 |
| Pelargonidin-3-O-galactoside-5-O-(6-O-ferulylglucoside) | 771 |
| Carnation AVIs | |
| Pelargonidin | 271 |
| Pelargonidin-3-O-glucoside | 433 |
| Pelargonidin-3,5-di-O-glucoside | 595 |

Figure 1:
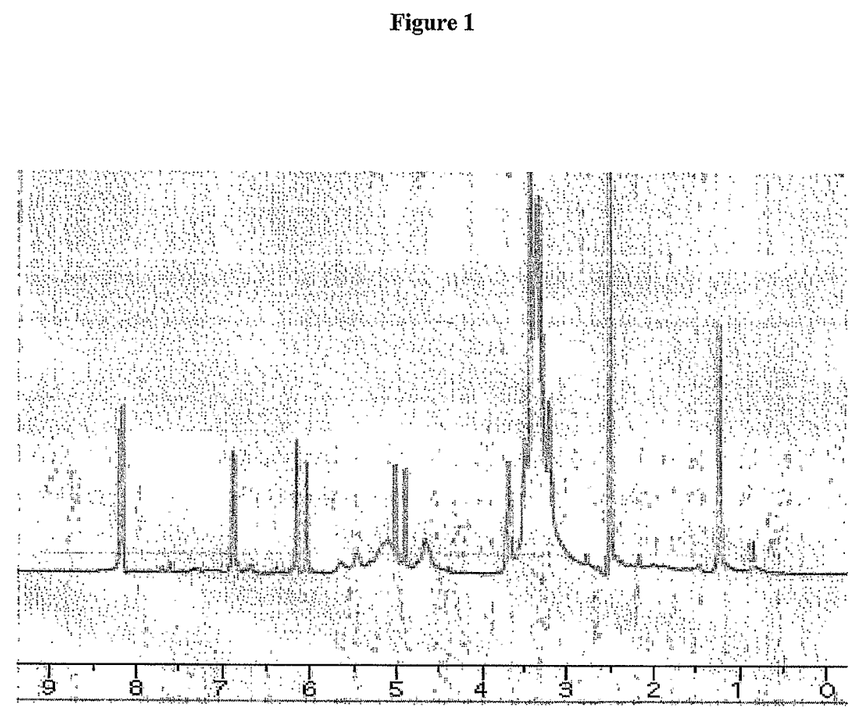
FIG. 1. NMR spectrum of carnation purified AVIs in DMSO solvent. The two peaks around chemical shift 1.0 ppm are from lipids present in AVIs. The major peaks between chemical shifts 2.0-9.0 ppm are from pelargonidin-3,5-diglucoside present in the AVIs.

Freeze dried carnation and lisianthus AVIs were separately dissolved in DMSO-D6 and subjected to NMR analysis. FIG. 1 shows a NMR spectrum clearly reflecting the presence of pelargonidin 3,5-diglucoside and another major component.

Lipid Analysis

To confirm the presence of lipids in the AVIs, lipids were isolated from both carnation and lisianthus AVIs using an organic solvent: chloroform:methanol:TFA (50:50:0.5 v:v:v). Freeze-dried AVIs were dissolved with the organic solvent. Subsequently, the organic solvent containing dissolved AVIs was partitioned against acidified water (water with 0.5% TFA). The process was repeated several times until no anthocyanic colour was obvious in the organic phase. The organic phase containing lipids was collected, and was subsequently dried under nitrogen to prepare lipids. The dried lipids were then dissolved in a chloroform (d4) and methanol to carry out NMR measurement.

Figure 2:
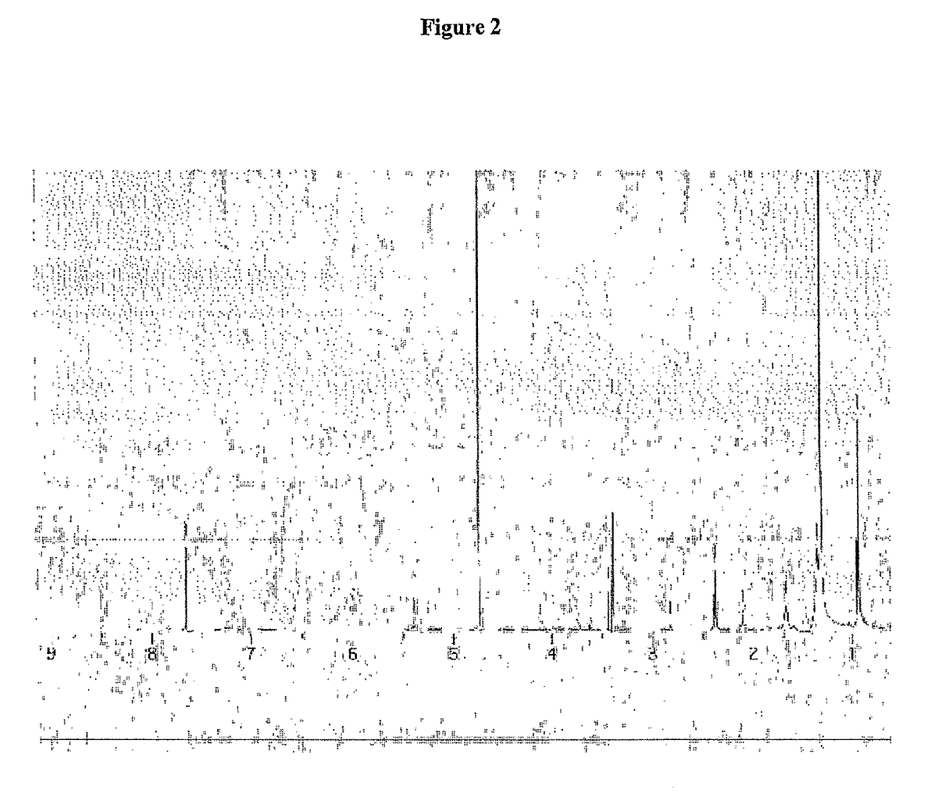
FIG. 2. NMR spectrum Of lipids isolated from carnation AVIs. The lipids were dissolved in a mixture of 50% methanol and 50% chloroform. The peaks at the chemical shifts of 3.4, 4.7 and 7.6 ppm are due to the solvents and all the rest reflect from the lipids.
Figure 3:
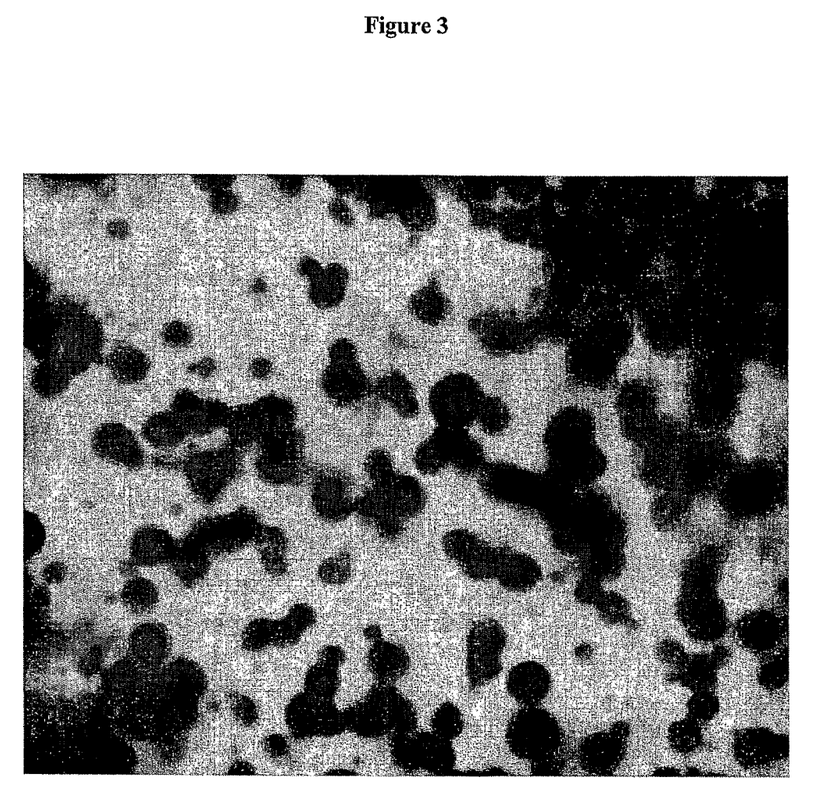
FIG. 3. In vitro reconstitution of carnation AVIs. Carnation AVIs were completely dissolved in DMSO. Subsequently DMSO was reduced to a minimum amount by vacuum drying at room temperature. In vitro AVIs/AVI-like structures were formed after the remaining liquid was mixed with water.
Figure 4:
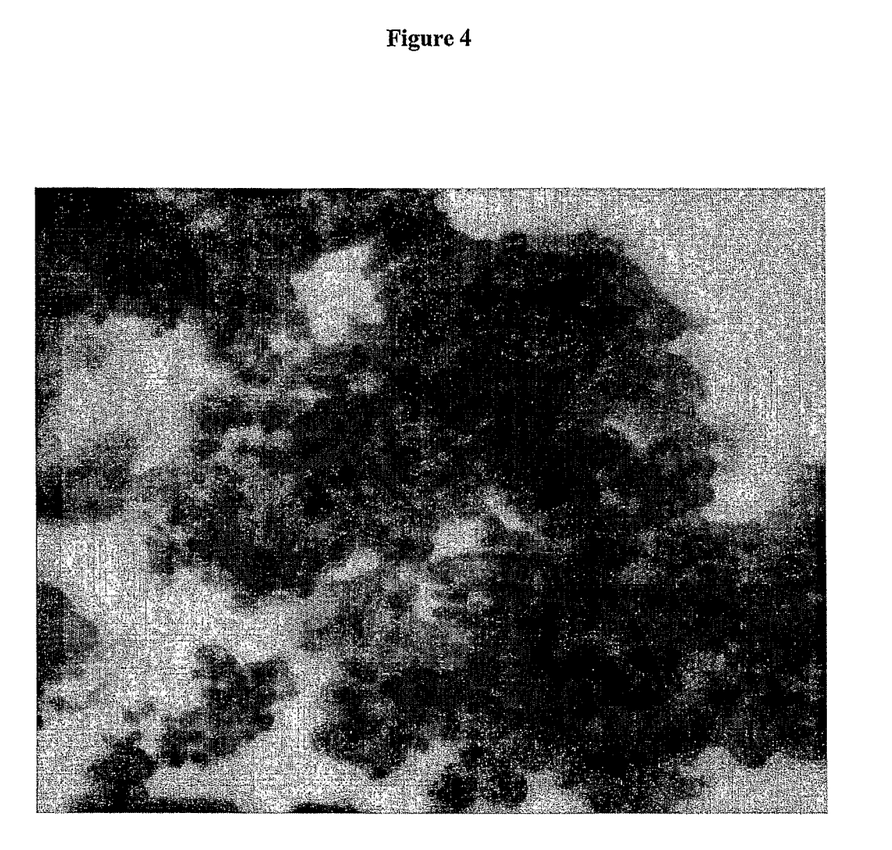
FIG. 4. In vitro reconstitution of purple lisianthus AVIs. Lisianthus AVIs were completely dissolved in DMSO. Subsequently DMSO was reduced to a minimum amount by vacuum drying at room temperature. In vitro AVIs/AVI-like structures were formed after the remaining liquid was mixed with water.

FIG. 2 shows the NMR spectrum of the extracted lipids from AVIs. Proton Nuclear Magnetic Resonance ($^1$H NMR) Spectroscopy of total lipids extracted from carnation AVIs displayed a typical upfield region of lipids extracted from a biological membrane sample (Kriat M, et al. 1993). The most prominent $^1$H NMR peak at 1.3 ppm is —$(CH_2)$n in fatty acyl chain. The peak at 0.9 ppm is characteristic of —$CH_3$ in fatty acyl chain. The peak at 1.6 ppm represents the bold italic H in the —CO—$CH_2$—$CH_2$; at 2.1 ppm $CH_2$CH=CH—; at 2.3 ppm —$CH_2$—COO—; at 2.8 ppm =CHCH$_2$CH— (polyunsaturated fatty acyl signal); at 3.6 ppm —$CH_2$—N+; at 5.4 ppm —CH=CH— in fatty acyl chain.

Example 3

In Vitro Preparation of AVIs/AVI-Like Structures Using Disassembled AVI Components Purified AVIs from the petals of carnation and lisianthus flowers were dissolved in pure DMSO. Subsequently, the DMSO solvent with dissolved AVIs was centrifuged to remove any insoluble materials. The resultant clear supernatants were dried down (to remove DMSO) through a vacuum drying process under room temperature (Speedvac). The samples were removed from the Speedvac when their volumes were about 50-100 μl (at this volume both AVI samples were slightly viscous).

Microscopic examination of these AVI-derived solutions did not show many AVIs (a small number of AVIs were produced as soon as a droplet of sample was placed on a glass slide). However, when an equal volume of 0.8 M acetic acid was added to the AVI-derived droplet on the glass slide, within a minute, numerous AVIs assembled. Initially small AVIs were formed, but gradually larger AVIs were formed.

The applicants found that adding water to these small volumes of AVI-derived samples in 1.5-mL tubes promoted the formation of AVIs. However, more AVI-like structures appeared to form in the presence of acetic acid on the glass slide, than in the water-added samples.

Example 4

Figure 5:
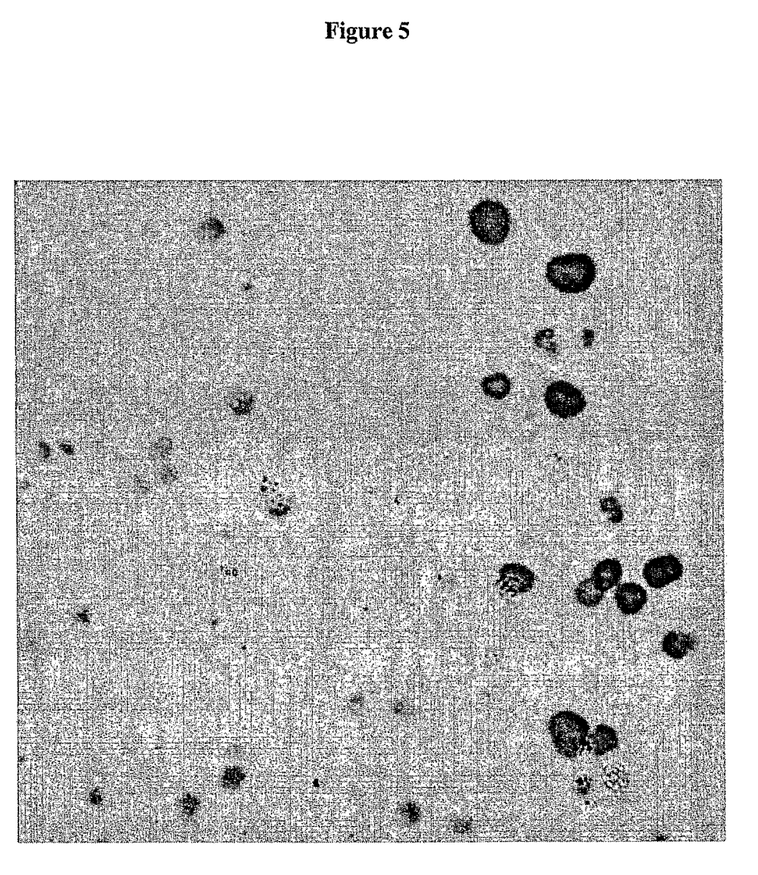
FIG. 5. In vitro formation of AVI-like structures from MGDG and pelargonidin 3-O-glucoside. Pelargonidin 3-O-glucoside and MGDG lipid were completely dissolved in DMSO, subsequently DMSO was reduced to minimum volume. In vitro formation of AVI-like structures was performed by mixing the remaining liquid with water containing sodium chloride.

In Vitro Formation of AVI-Like Structures by Combining an Anthocyanin and a Lipid In vitro formation AVI-like structures using defined compounds was realized using pelargonidin-3-glucoside (Pel-3-G) isolated from *Rhabdothamnus solandri* and monoglacto diglyceride (MGDG). Around 1 mg of Pel-3-G and 1 mg of MGDG were mixed and dissolved in 30 microlitres of DMSO. Subsequently, the well dissolved anthocyanin and lipid were vacuum-dried to about 10 microlitres of volume: To form AVIs in vitro, 10 µL of the mixture (Pel-3-G and MGDG) was mixed with 2 µL of 0.5 M sodium chloride and 5 µL of miliQ water. After mixing, 5-10 µL of the final mixture was placed on a glass slide to observe AVI formation. FIG. 5 shows the AVIs formed using this approach.

The above examples illustrate practice of the invention. It will be well understood by those skilled in the art that numerous variations and modifications may be made without departing from the spirit and scope of the invention.

REFERENCES

Andersen, M. and M. Jordheim 2006. The anthocyanins. In Flavonoids: chemistry, biochemistry and applications Eds. A. M. O. and K. R. Markham. CRC Press. 471-551 pp.

Asen, S., Stewart, R. N., Norris, K. H., 1975. Anthocyanin, flavonol co pigments, and pH responsible for larkspur flower colour. Phytochemistry 14, 2677-2682.

Biomembrane Protocols: 1993 I. Isolation and Analysis Series: Methods in Molecular Biology, Vol. 19 Graham, John M., Higgins, Joan A. 1993, 336 p. Humana Press ISBN: 978-0-89603-236-1.

Bligh, E G and Dyer, W J 1959 A Rapid Method Of Total Lipid Extraction And Purification. Canadian Journal Of Biochemistry And Physiology. 37:911-917.

Carrapiso, A I and Garcia, C. 2000 Development in lipid analysis: Some new extraction techniques and in situ transesterification. LIPIDS 35:1167-1177.

Cormier, F., Do, C. B., 1993. XXVII *Vitis vinifera* L. (grapevine): in vitro production of anthocyanins. In: Bajaj, Y. P. S. (Ed), Biotechnology in Agriculture and Forestry, Vol. 24, Medicinal and Aromatic Plants, V. Springer Verlag, Berlin, pp. 373-386.

Douliez, J P; Gaillard, C; Navailles, L, et al. 2006 Novel lipid system forming hollow microtubes at high yields and concentration Langmuir 22: 2942-2945.

Gonnet J-F., 2003. Origin of the Color of Cv. Rhapsody in Blue Rose and Some Other So-called "Blue" Roses. J. Agric. Food Chem., 51, 4990-4994.

Hemleben, V., 1981. Anthocyanin carrying structures in specific genotypes of *Matthiola incana* R. Br. Z. Naturforsch 36c, 926-927.

Kubo, H., Nozue, M., Kawasaki, K., Yauda, H., 1995. Intravacuolar spherical bodies in *Polygonium cuspidatum*. Plant Cell Physiol. 36, 1453-1458.

Liang, M T; Davies, N M; Toth, I 2005 Encapsulation of lipopeptides within liposomes: Effect of number of lipid chains, chain length and method of liposome preparation International Journal Of Pharmaceutics. 301: 247-254.

Markham, K. R., S. J. Bloor, R. Nicholson, R. Rivera, M. Shemluck, P. G. Kevan and C. Michener 2004. Black flower coloration in wild *Lisianthius nigrescens*: Its chemistry and ecological consequences. Zeitschrift Fur Naturforschung Section C-a Journal of Biosciences. 59:625-630.

Markham, K. R., K. S. Gould, C. S. Winefield, K. A. Mitchell, S. J. Bloor and M. R. Boase 2000. Anthocyanic vacuolar inclusions—their nature and significance in flower colouration. Phytochemistry. 55:327-36.

Markham J E, Li J, Cahoon E B, Jaworski J G 2006 Separation and identification of major plant sphingolipid classes from leaves. J. Biol Chem 281:22684-94.

Nozzolillo, C., Ishikura, N., 1988. An investigation of the intracellular site of anthocyanins using isolated protoplasts and vacuoles. Plant Cell Rep. 7, 389.

Nozue, M., Kubo, H., Nishimura, M., Yasuda, H., 1995. Detection and characterization of a vacuolar protein (VP24) in anthocyanin-producing cells of sweet potato in suspension culture. Plant Cell Physiol. 36, 883-889.

Small C. J., Pecket, R. C., 1982. The ultrastructure in anthocyanoplasts in red-cabbage. Planta 154, 97-99.

Zhang et al., 2006, New insight into the structures and formation of anthocyanic vacuolar inclusions in flower petals. BMC Plant Biology 6, Art 29.

The invention claimed is:

1. A method for in vitro formation of an irregular and aggregated anthocyanic vacuolar inclusion (AVI)-like structure, the method comprising the step of concentrating a solution comprising at least one anthocyanin and at least one lipid dissolved in a solvent, by removing a portion of the solvent, so that the AVI-like structure is formed in vitro.

2. The method of claim 1 in which the solvent is a polar aprotic solvent.

3. The method of claim 2 in which the polar aprotic solvent is selected from the group consisting of dimethyl sulfoxide, dimethylformamide, dioxane, hexamethylphosphorotriamide, and tetrahydrofuran.

4. The method of claim 1 in which the solvent is a mixture of chloroform and methanol.

5. The method of claim 1 in which the solvent is a mixture of chloroform and ethanol.

6. The method of claim 1 in which the solvent is DMSO.

7. The method of claim 1 in which pH of the solvent is optimised.

8. The method of claim 1 in which the AVI-like structure is formed in an aqueous solution.

9. The method of claim 1 in which the AVI-like structure is formed in a lipid-based environment.

10. The method of claim 1 in which the AVI-like structure is formed in an acid-based solution.

* * * * *

UNITED STATES PATENT AND TRADEMARK OFFICE
CERTIFICATE OF CORRECTION

PATENT NO.       : 8,648,049 B2                                           Page 1 of 1
APPLICATION NO.  : 13/265026
DATED            : February 11, 2014
INVENTOR(S)      : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this

Twenty-ninth Day of September, 2015

Michelle K. Lee
*Director of the United States Patent and Trademark Office*